United States Patent
Kim et al.

(10) Patent No.: US 10,213,218 B2
(45) Date of Patent: Feb. 26, 2019

(54) SLEEVE PIN ASSEMBLY FOR FIXING BONE PIECES

(71) Applicant: SOLCO BIOMEDICAL CO., LTD., Pyeongtaek-si (KR)

(72) Inventors: Il Kim, Seoul (KR); Myung Heon Ha, Osan-si (KR)

(73) Assignee: SOLCO BIOMEDICAL CO., LTD., Pyeongtaek-si (KR)

( * ) Notice: Subject to any disclaimer, the term of this patent is extended or adjusted under 35 U.S.C. 154(b) by 0 days.

(21) Appl. No.: 15/716,746

(22) Filed: Sep. 27, 2017

(65) Prior Publication Data

US 2019/0021747 A1  Jan. 24, 2019

(30) Foreign Application Priority Data

Jul. 18, 2017  (KR) .................... 10-2017-0091084

(51) Int. Cl.
*A61B 17/56* (2006.01)
*A61B 17/17* (2006.01)
*A61B 17/72* (2006.01)

(52) U.S. Cl.
CPC ........ *A61B 17/1717* (2013.01); *A61B 17/171* (2013.01); *A61B 17/1739* (2013.01); *A61B 17/7225* (2013.01)

(58) Field of Classification Search
CPC .............. A61B 17/1717; A61B 17/171; A61B 17/1739; A61B 17/7225
USPC ...................................................... 606/62, 80
See application file for complete search history.

(56) References Cited

U.S. PATENT DOCUMENTS

| | | | | |
|---|---|---|---|---|
| 3,351,054 A | * | 11/1967 | Florek | A61B 17/1686 606/104 |
| 4,157,714 A | * | 6/1979 | Foltz | A61B 17/1628 408/228 |
| 4,341,206 A | * | 7/1982 | Perrett | A61B 17/1721 606/102 |
| 2004/0127907 A1 | * | 7/2004 | Dakin | A61B 17/683 606/62 |
| 2013/0245629 A1 | * | 9/2013 | Xie | A61B 17/162 606/80 |
| 2013/0338669 A1 | * | 12/2013 | Brianza | A61B 5/4509 606/80 |
| 2014/0142715 A1 | | 5/2014 | McCormick | |
| 2017/0079699 A1 | * | 3/2017 | Fallin | A61B 17/1725 |

FOREIGN PATENT DOCUMENTS

| | | | |
|---|---|---|---|
| JP | 2007512100 A | | 5/2007 |
| JP | 2009273598 A | | 11/2009 |
| JP | 2015100473 A | | 6/2015 |
| KR | 10-2015-0143130 A | | 12/2015 |

* cited by examiner

*Primary Examiner* — Pedro Philogene
*Assistant Examiner* — David C Comstock
(74) *Attorney, Agent, or Firm* — Dilworth IP, LLC

(57) ABSTRACT

A sleeve pin assembly for fixing a bone piece, and more particularly, a new structure of sleeve pin assembly for fixing a bone piece in which a pin for fixing a plurality of bone pieces that have occurred upon being fractured is coupled to a sleeve with a collet method is provided. The sleeve pin assembly for fixing a bone piece includes: a pin having a fixing portion; a collet portion detachably coupled to the pin; a fastening portion having one end connected to the collet portion and the other end that can be fastened to an electric drill; and a sleeve including an internal receiving space to receive the collet portion.

6 Claims, 3 Drawing Sheets

SLEEVE PIN ASSEMBLY FOR FIXING BONE PIECES

FIELD OF THE INVENTION

The present invention relates to a sleeve pin assembly for fixing a bone piece, and more particularly, to a new structure of sleeve pin assembly for fixing a bone piece in which a pin for fixing a plurality of bone pieces that have occurred upon being fractured is coupled to a sleeve with a collet method.

BACKGROUND OF THE INVENTION

A fracture indicates a state in which continuity of a bone, an epiphyseal plate, or a joint surface is completely or incompletely lost and generally occurs by an external force. A fracture may be divided into a simple fracture and a crush fracture according to the number of fractured bone pieces. A simple fracture indicates a case in which two fractured bone pieces occur by one fracture line, and a crush fracture indicates a case in which three or more fractured bone pieces occur by two or more fracture lines. In an injury having a fracture such as a joint peripheral fracture and a crush fracture, a plurality of bone pieces may occur.

In order to treat such a fracture portion, an external splintage method of vertically inserting a pin from the outside to the fracture portion and fixing the fracture portion using plaster and an internal fixation method of directly penetrating and inserting a pin into the fracture portion are used.

Recently, as a method of using an internal fixing device, Korean Patent Laid-Open Publication No. 10-2015-0143130 is well known. In Korean Patent Laid-Open Publication No. 10-2015-0143130, an internal fixing pin and an external fixing pin are inserted into a bone piece, a fractured bone is fixed, the internal fixing pin is removed, and a separate metal nail is inserted.

However, Korean Patent Laid-Open Publication No. 10-2015-0143130 has problems that a secure fixing work cannot be performed with only a pin inserted into the bone piece and that a separate drilling hole should be processed in order to fasten the external fixing pin to a cortex of a bone and that a complex process of inserting or removing a spacer should be performed for accurate drilling.

PRIOR ART DOCUMENT

Patent Document (Patent document 1) Korean Patent Laid-Open Publication No. 10-2015-0143130.

SUMMARY OF THE INVENTION

The present invention has been made in view of the above problems and provides a sleeve pin assembly for fixing a bone piece that can perform accurate drilling in order to securely fix a plurality of bone pieces and to transfer a movement of a sleeve pin in only an axial direction upon performing a drilling operation and that can be easily separated in order to insert only a sleeve pin into a fracture portion after drilling.

In accordance with an aspect of the present invention, a sleeve pin assembly for fixing a bone piece includes a pin having a fixing portion; a collet portion detachably coupled to the pin; a fastening portion having one end connected to the collet portion and the other end that can be fastened to an electric drill; and a sleeve including an internal receiving space to receive the collet portion.

The collet portion may include a pin coupler detachably coupled to the pin; and a sleeve coupler connected to the pin coupler and coupled to the sleeve.

The pin coupler of the collet portion may have a detachment groove that receives a fixing portion of the pin, wherein a shape of the detachment groove may be changed according to a coupling level of the sleeve and the collet portion.

An outer circumferential surface of the pin coupler of the collet portion may be inclined and have a gap slit cut in a rotation axis direction, and a gap of the gap slit may change according to a coupling level of the sleeve and the collet portion.

At an inner circumferential surface of the sleeve, an inclined surface may be formed to correspond to the outer circumferential surface of the pin coupler of the collet portion.

At an inner circumferential surface of the sleeve, a screw may be formed to correspond to an outer circumferential surface of the sleeve coupler of the collet portion, and the collet portion and the sleeve may be coupled by a screw.

The fixing portion of the pin may have a through-hole that penetrates a cable.

DETAILED DESCRIPTION OF THE INVENTION

Hereinafter, a sleeve pin assembly for fixing a bone piece according to an exemplary embodiment of the present invention will be described in detail with reference to the drawings. The terms used hereinafter should not be construed as limited to general or dictionary meanings, and in order for an inventor to describe the invention with a best method, the invention should be construed with meanings and concepts corresponding to the spirit of the present invention based on a principle that can appropriately define concepts of terms.

Figure 1:
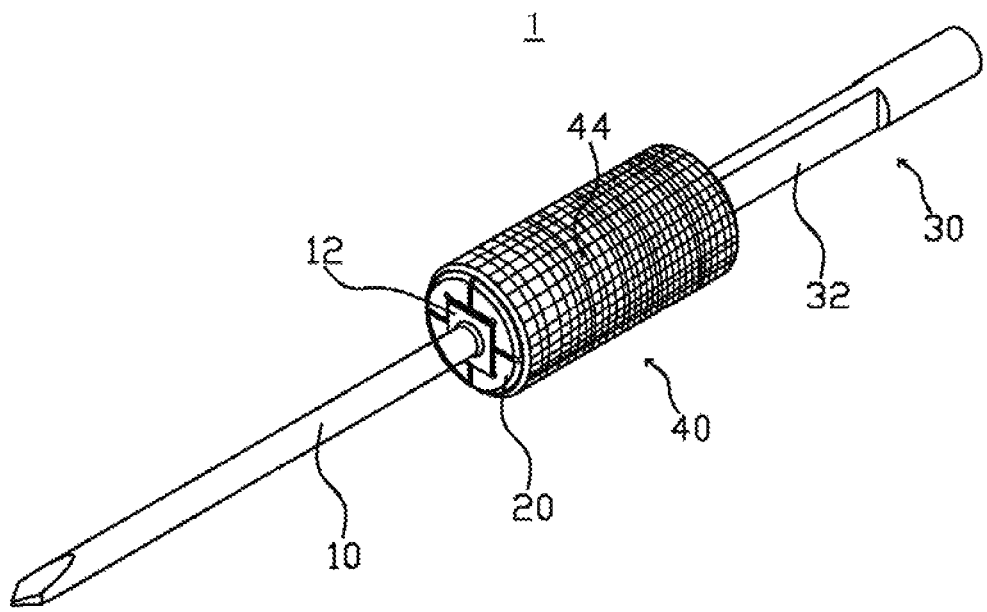
FIG. 1 is a perspective view illustrating an assembled state of a sleeve pin assembly for fixing a bone piece according to an exemplary embodiment of the present invention.
Figure 2:
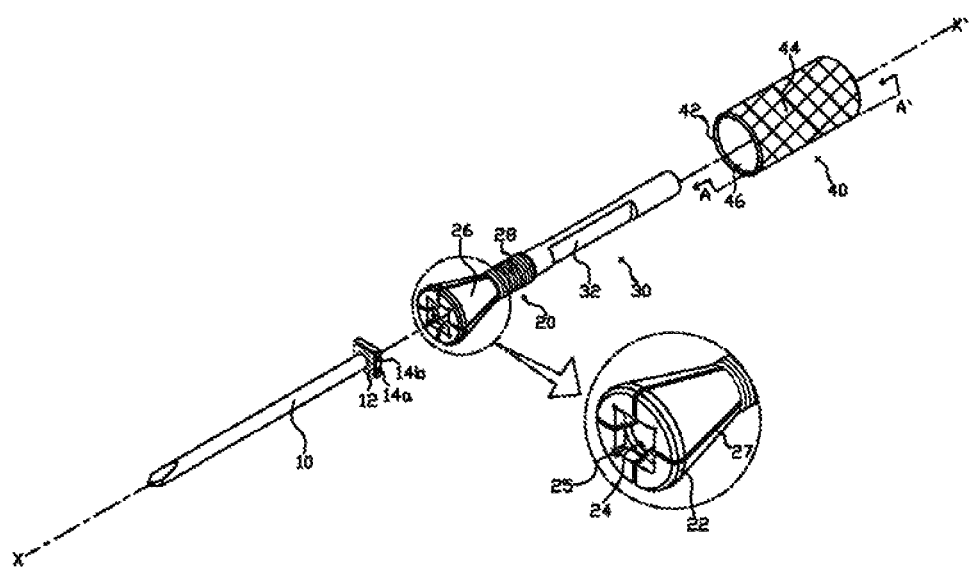
FIG. 2 is an exploded perspective view illustrating a disassembled state of a sleeve pin assembly for fixing a bone piece according to an exemplary embodiment of the present invention.

FIG. 1 is a perspective view illustrating an assembled state of a sleeve pin assembly for fixing a bone piece according to an exemplary embodiment of the present invention, and FIG. 2 is an exploded perspective view illustrating a disassembled state of a sleeve pin assembly for fixing a bone piece according to an exemplary embodiment of the present invention.

Referring to FIGS. 1 and 2, a bone piece fixing sleeve pin assembly 1 used when fixing fractured bone pieces in an original bone shape includes a pin 10, a collet portion 20, an electric drill fastening portion 30, and a sleeve 40.

In the bone piece fixing sleeve pin assembly 1 according to the present exemplary embodiment, the pin 10 is inserted into a fracture portion of a bone. The pin 10 may be made of a material inserted into the bone piece to have strength to fix the bone pieces and the material of the pin 10 is not limited thereto.

At one end of the pin 10, a fixing portion 12 formed integrally with the pin 10 to be inserted into the collet portion 20 is formed.

The collet portion 20 is configured with a rotation body rotating about the same rotation axis X-X' as that of the pin 10 and includes a pin coupler 26 and a sleeve coupler 28.

At a side surface of the pin coupler 26 of the collet portion 20, a detachment groove 24 that inserts and couples the fixing portion 12 of the pin 10 is provided. As shown in FIG. 2, the detachment groove 24 is configured in a shape corresponding to that of the fixing portion 12. Due to such a detachment groove 24, the fixing portion 12 integrally formed with the pin 10 is inserted or drawn out. As shown in FIG. 2, a shape of the fixing portion 12 is shown in a cuboid, but it is not limited thereto and may be configured in another shape that can be detachably attached to the collet portion 20 to be described later.

A detachment auxiliary portion 25 cut in a cylindrical shape using a corner formed in a direction of the rotation axis X-X' of the detachment groove 24 as a shaft is provided. When a corner in a direction of the rotation axis X-X' of the fixing portion 12 is inserted into or is drawn out from the detachment auxiliary portion 25, a latch phenomenon or a corner abrasion phenomenon is prevented and thus the detachment auxiliary portion 25 performs a function of easily assisting detachment performed between the fixing portion 12 and the detachment groove 24.

At an outer circumferential surface of the pin coupler 26 of the collet portion 20, an inclined surface inclined from one end to the other end of the collet portion 20 is formed, and at an outer circumferential surface of the sleeve coupler 28, a male screw surface extended parallel to the other end direction of the collet portion 20 along the rotation axis X-X' in a portion contacting with the pin coupler 26 and having a male screw is formed. Further, in a portion enclosing the detachment groove 24 among an outer circumferential surface of the pin coupler 26, a pressing maintaining surface 22 extended while maintaining a predetermined circumference is formed.

In the pin coupler 26 of the collet portion 20, a gap slit 27 cut in a slit form in a direction of the rotation axis X-X' is arranged with separated by a predetermined gap in a circumference direction of the pin coupler 26. Due to such a gap slit 27, a shape of the pin coupler 26 is divided into several partitions, and partitions are separated by a predetermined gap. FIG. 2 illustrates a shape in which the pin coupler 26 is separated into four partitions.

In order to have the same rotation axis X-X', one end of the electric drill fastening portion 30 is connected to the collet portion 20 to be integrally formed, and the other end of the fastening portion 30 is fastened to an electric drill (not shown). When the other end of the fastening portion 30 is inserted into the electric drill, a lock member (not shown) provided within the electric drill is inserted into a fastening groove 32 formed in the fastening portion 30 to perform a lock operation. In contrast, when the lock member is drawn out from the fastening groove 32, the lock operation is released. Such lock and release operations may be easily performed by a mechanical or electric manipulation of the electric drill.

In order to receive the collet portion 20, the sleeve 40 is formed in a cylindrical shape having a hollow and includes a pin pressing portion 46 and a collet coupler 48. When the collet portion 20 is received within the sleeve 40, a rotation axis X-X' of the collet portion 20 corresponds with that of the sleeve 40, and an outer circumferential surface of the collet portion 20 may contact an inner circumferential surface of the sleeve 40.

Figure 3:
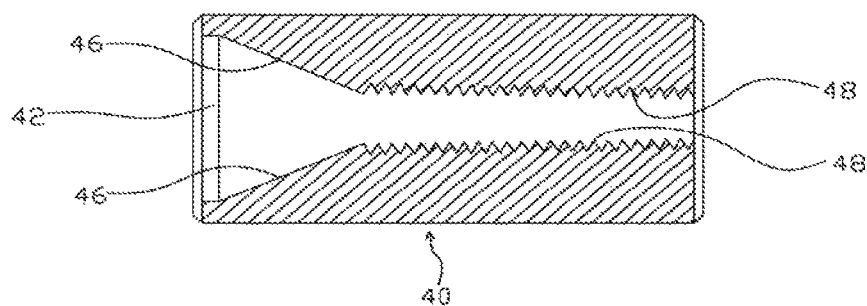
FIG. 3 is a cross-sectional view illustrating the sleeve pin assembly taken along line A-A' of FIG. 2.

FIG. 3 is a cross-sectional view illustrating the sleeve pin assembly taken along line A-A' of FIG. 2.

Specifically, referring to FIG. 3, at an inner circumferential surface of the pin pressing portion 46 of the sleeve 40, an inclined surface corresponding to an outer circumferential surface of the pin coupler 26 of the collet portion 20 is formed, and at an inner circumferential surface of the collet coupler 48, a female screw is provided to correspond to an outer circumferential surface of the sleeve coupler 28 of the collet portion 20 and thus a female screw surface extended to be parallel is formed. Further, in a predetermined portion of an inner circumferential surface of the pin pressing portion 46, a pressing maintaining corresponding surface 42 corresponding to the pressing maintaining surface 22 of the pin coupler 26 is formed. Therefore, an inner circumferential surface of the sleeve 40 and an outer circumferential surface of the collet portion 20 contact to mutually correspond.

In order to easily move the sleeve 40, at an outer circumferential surface of the sleeve 40, a protrusion and depression portion 44 that enables a worker to hold without sliding is formed.

A process of receiving the collet portion 20 in the sleeve 40 is as follows.

The sleeve 40 and the collet portion 20 are coupled by a screw, and a coupling level of the sleeve 40 and the collet portion 20 is changed according to a rotation movement.

Figure 4:
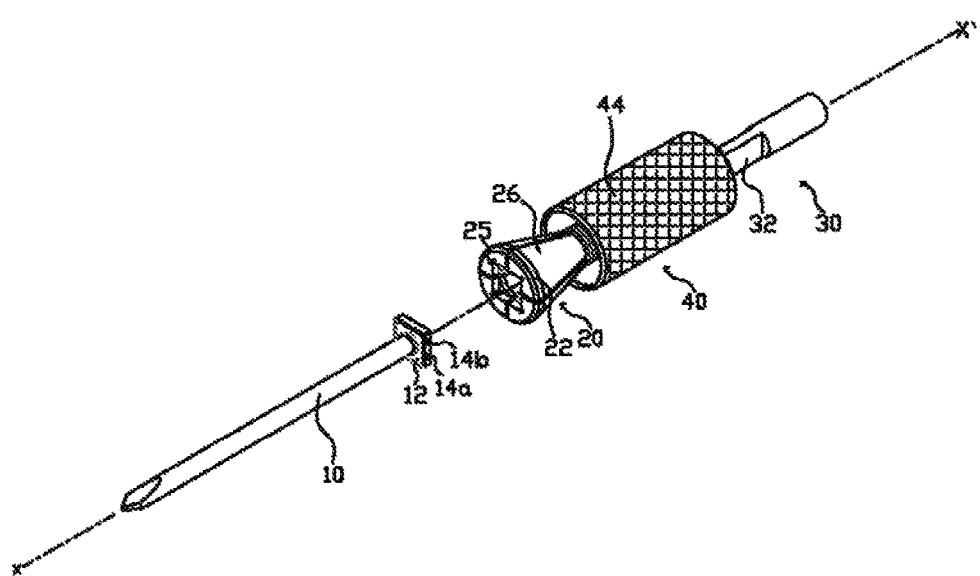
FIG. 4 is a perspective view illustrating a state in which a pin of FIG. 1 is separated from a collet portion.
Figure 5:
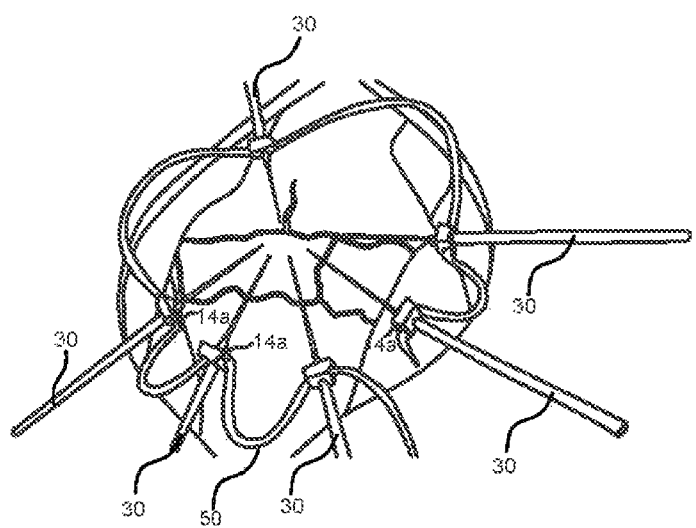
FIG. 5 is a diagram illustrating a state in which a plurality of pins are coupled by a cable.

FIG. 4 is a perspective view illustrating a state in which a pin of FIG. 1 is separated from a collet portion, and FIG. 5 is a diagram illustrating a state in which a plurality of pins are coupled by a cable.

Referring to FIG. 4, by inserting the pin pressing portion 46 of the sleeve 40 into the other end of the fastening portion 30, the collet portion 20 connected to the fastening portion 30 is received into the sleeve 40. After the collet portion 20 is received into the sleeve 40, when the sleeve 40 is rotated in one direction, the sleeve coupler 28 having a male screw surface of the collet portion 20 contacts (hereinafter, referred to as a decompression position) the collet coupler 48 having a female screw surface of the sleeve 40 and is coupled by a screw to the collet coupler 48.

While the sleeve 40 and the collet portion 20 are coupled by a screw, the sleeve 40 continues to move and stops moving at a point (hereinafter, referred to as a pressing position) in which the pressing maintaining corresponding surface 42 completely contacts with the pressing maintaining surface 22. In contrast, after the sleeve 40 and the collet portion 20 are coupled by a screw, when the sleeve 40 rotates at a pressing position in the other direction, while screw coupling to the collet portion 20 is released, the sleeve 40 is moved to a decompression position.

When the sleeve 40 is disposed at a decompression position, an external diameter of the pressing maintaining surface 22 is larger than an internal diameter of the pressing maintaining corresponding surface 42. Because the sleeve 40 moves from a decompression position to a pressing position, when a movement of the sleeve 40 is stopped, an external diameter of the pressing maintaining surface 22 corresponds with an inner diameter of the pressing maintaining corresponding surface 42. At a position in which the pressing maintaining surface 22 corresponds with the pressing maintaining corresponding surface 42, a force in which the sleeve 40 presses the collet portion 20 is constantly maintained and thus pressing may be maintained.

A process of detaching the fixing portion 12 from the collet portion 20 is as follows.

When the sleeve 40 is moved from a decompression position to a pressing position, the sleeve 40 presses the pin coupler 26 of the collet portion 20, and when a gap of each partition of the pin coupler 26 divided by the gap slit 27 gradually decreases, the detachment groove 24 formed in the pin coupler 26 reduces. Therefore, the fixing portion 12 inserted into the detachment groove 24 is pressed to be completely fixed to the collet portion 20.

In contrast, when the sleeve 40 is moved from a pressing position to a decompression position, the sleeve 40 decompresses the pressed pin coupler 26, a reduced partition gap of the pin coupler 26 gradually increases and thus the detachment groove 24 increases. Therefore, pressing of the fixing portion 12 inserted into the detachment groove 24 may be released and thus the fixing portion 12 is separated from the collet portion 20. Therefore, a detachment work of the pin 10 connected to the fixing portion 12 may be smoothly performed with a simple manipulation of the sleeve 40.

In a state in which the sleeve 40 is positioned to press with the collet portion 20, the fixing portion 12, the collet portion 20, the fastening portion 30, and the sleeve 40 configure the bone piece fixing sleeve pin assembly 1 while having the same rotation axis X-X. When the fastening portion 30 of such an assembly 1 is fastened to an electric drill (not shown) having the same rotation axis X-X', rotatory power of the electric drill (not shown) is transferred only in a direction of the axis X-X' of the pin 10 and thus an accurate drilling work without shaking is guaranteed.

In the fixing portion 12 of the bone piece fixing sleeve pin assembly 1 according to an exemplary embodiment of the present invention, through-holes 14a and 14b are provided to insert a cable for performing a fixing work of the bone piece.

In order to restore bone pieces in an original bone shape, a fixing work of the bone pieces is performed, and a secure fixing work cannot performed with only the pin 10 inserted into the bone pieces. For example, when a knee joint is divided into a plurality of bone pieces, a problem occurs that bone pieces are separated from an original bone shape with only a work of bonding the knee joint in an original joint shape and inserting the pin 10. In order to solve such a problem, in the present exemplary embodiment, the pin 10 has through-holes 14a and 14b for inserting a cable 50 for performing a fixing work of the bone pieces, and as shown in FIG. 5, by connecting a plurality of pins 10 inserted into a plurality of bone pieces with a cable inserted into the through-holes 14a and 14b, the entire bone pieces may be bound and thus a bone piece fixing work can be securely performed.

Hereinafter, an operation process using the bone piece fixing sleeve pin assembly 1 according to an exemplary embodiment of the present invention will be described.

First, a worker (operator) inserts the collet portion 20 to a decompression position within the sleeve 40. In this state, after the fixing portion 12 of the pin 10 is inserted into the detachment groove 24 of the collet portion 20, when the sleeve 40 is moved to a pressing position by rotating in one direction, the fixing portion 12 inserted into the detachment groove 24 is fixed. Assembly of the sleeve pin 10 for fixing the bone piece is complete in a state illustrated in FIG. 1 by such a process.

After assembly is complete, the worker fastens the fastening portion 30 of the assembly 1 to the electric drill (not shown) and inserts the pin 10 into a portion in which bone pieces are formed using rotatory power of the electric drill. When the pin 10 is inserted to a desired position, the worker manipulates the electric drill to release fastening between the assembly 1 and the electric drill.

After fastening between the assembly 1 and electric drill is released, when the worker rotates the sleeve 40 in the other direction and moves the sleeve 40 to a decompression position, fixing between the fixing portion 12 of the pin 10 and the detachment groove 24 is released and thus while the sleeve 40 and the collet portion 20 are separated, only the pin 10 may be inserted into the bone piece.

After a plurality of pins 10 are inserted into the bone piece, the worker inserts a cable through the through-holes 14a and 14b provided in the fixing portion 12 to connect each of a plurality of pins 10. When the cable 50 is connected to bind the entire of a plurality of bone pieces in an original bone shape, the worker performs a work of cutting the unnecessary cable 50.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

According to a sleeve pin assembly for fixing a bone piece of the present invention, when using a pin in order to fix a fracture portion, a detachment work of the pin connected to a fixing portion with a simple manipulation of a sleeve can be smoothly performed.

Further, according to the present invention, when a sleeve pin is fastened to an electric drill, rotatory power of the electric drill is transferred only to an axial direction of the pin and thus accurate drilling work can be performed without shaking.

Further, according to the present invention, a plurality of pins inserted into a plurality of bone pieces are connected to a cable inserted into a through-hole and thus the bone piece can be entirely bound and a bone piece fixing work can be thus securely performed.

We claim:

1. A sleeve pin assembly for fixing a plurality of bone pieces, the sleeve pin assembly comprising:
    a pin having a fixing portion;
    a collet portion detachably coupled to the pin;
    a fastening portion having one end connected to the collet portion and the other end that can be fastened to an electric drill; and
    a sleeve comprising an internal receiving space to receive the collet portion
    wherein the fixing portion of the pin has a through-hole that penetrates a cable, and wherein a plurality of the pins inserted into the plurality of bone pieces are connected to the cable inserted into the through holes.

2. The sleeve pin assembly of claim 1, wherein the collet portion comprises:
    a pin coupler detachably coupled to the pin; and
    a sleeve coupler connected to the pin coupler and coupled to the sleeve.

3. The sleeve pin assembly of claim 2, wherein the pin coupler of the collet portion has a detachment groove that receives a fixing portion of the pin,
 wherein a shape of the detachment groove is changed according to a coupling level of the sleeve and the collet portion.

4. The sleeve pin assembly of claim 2, wherein an outer circumferential surface of the pin coupler of the collet portion is inclined and has a gap slit cut in a rotation axis direction, and
 a gap of the gap slit changes according to a coupling level of the sleeve and the collet portion.

5. The sleeve pin assembly of claim 4, wherein at an inner circumferential surface of the sleeve, an inclined surface is formed to correspond to the outer circumferential surface of the pin coupler of the collet portion.

6. The sleeve pin assembly of claim 2, wherein at an inner circumferential surface of the sleeve, a screw is formed to correspond to an outer circumferential surface of the sleeve coupler of the collet portion, and
 the collet portion and the sleeve are coupled by a screw.

* * * * *